United States Patent

Baranzahi et al.

Patent Number: 6,109,094
Date of Patent: *Aug. 29, 2000

[54] METHOD AND DEVICE FOR GAS SENSING

[75] Inventors: Amir Baranzahi; Ingemar Lundström; Anita Lloyd Spetz, all of Linköping, Sweden

[73] Assignee: Forskarpatent I Linkoping Ab, Linkoping, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/809,905

[22] PCT Filed: Sep. 22, 1995

[86] PCT No.: PCT/SE95/01084

§ 371 Date: Jun. 19, 1997

§ 102(e) Date: Jun. 19, 1997

[87] PCT Pub. No.: WO96/09534

PCT Pub. Date: Mar. 28, 1996

[30] Foreign Application Priority Data

Sep. 23, 1994 [SE] Sweden ................................ 94013218

[51] Int. Cl.[7] ............................. G01N 7/00; G01N 31/12; H01L 27/14
[52] U.S. Cl. ............................. 73/31.06; 257/414; 422/94
[58] Field of Search ............................. 73/31.06; 338/34; 422/98, 94; 257/414, 382; 204/424

[56] References Cited

U.S. PATENT DOCUMENTS

| 3,699,803 | 10/1972 | Sumi et al. . |
| 4,322,383 | 3/1982 | Yasuda et al. . |
| 4,337,476 | 6/1982 | Fraser et al. . |
| 4,816,888 | 3/1989 | Tanaka et al. . |
| 4,875,083 | 10/1989 | Palmour . |
| 4,885,929 | 12/1989 | Kasahara et al. ...................... 73/31.06 |
| 4,897,628 | 1/1990 | Ippommatsu et al. .................... 338/34 |
| 4,911,892 | 3/1990 | Grace et al. ............................. 422/94 |
| 4,931,851 | 6/1990 | Sibbald et al. .......................... 257/414 |
| 5,147,523 | 9/1992 | Yagawara et al. ...................... 204/424 |
| 5,154,514 | 10/1992 | Gambino et al. . |
| 5,250,170 | 10/1993 | Yagawara et al. ...................... 204/431 |
| 5,251,470 | 10/1993 | Lampe et al. . |
| 5,273,779 | 12/1993 | Chen et al. . |
| 5,285,084 | 2/1994 | von Windheim et al. . |
| 5,323,022 | 6/1994 | Glass et al. . |
| 5,384,470 | 1/1995 | Tachibana et al. ....................... 257/77 |
| 5,401,470 | 3/1995 | Poli . |

FOREIGN PATENT DOCUMENTS

| 488 352 | 6/1992 | European Pat. Off. . |
| 635 717 | 1/1995 | European Pat. Off. . |
| 42 23 432 | 2/1993 | Germany . |
| 665 908 | 6/1988 | Switzerland . |
| 94/27139 | 11/1994 | WIPO . |

*Primary Examiner*—Hezron Williams
*Assistant Examiner*—Jay L. Politzer
*Attorney, Agent, or Firm*—Pillsbury Madison & Sutro LLP

[57] ABSTRACT

A gas sensing device having a semiconductor substrate, wherein the semiconductor substrate is covered by an insulator layer, on which an intermediate layer is formed, and subsequently covered by a gas sensing catalytic layer, wherein the intermediate layer and the catalytic layer are made of different materials. The gas sensing device may optionally have dispersed between the insulator layer and the intermediate layer a catalytic metal layer. The gas sensing device provides improved stability and speed of response, even when used at high ambient temperatures, such as temperatures found in combustion systems. A method for making the gas sensing device is also disclosed.

22 Claims, 2 Drawing Sheets

METHOD AND DEVICE FOR GAS SENSING

This application is the national phase of international application PCT/SE95/01084, filed Sep. 22 1995 which designated the U.S.

TECHNICAL FIELD

The present invention relates to a method and a device for gas sensing and particularly for gas sensing at high ambient temperatures.

PRIOR ART

It is known that catalytic metals can be used as gates for gas sensitive field effect devices (transistors, capacitors, diodes, etc). Thus they comprise metal-insulator-semiconductor- or metal-semiconductor structures. Such devices may be used to measure small concentrations of molecules like hydrogen, hydrogen sulfide, alcohols, hydrocarbons, ammonia, amines, etc. The highest operation temperature is determined by the semiconductors used, which e.g. for silicon is about 250° C. but for silicon carbide about 1000° C.

The gas sensitivity occurs because reaction intermediaries (like hydrogen atoms) give rise to electrical phenomena at the metal-insulator or metal-semiconductor interface, which changes the electric field outside the semiconductor. In FIG. 1 is demonstrated, in a simple cross section, a structure of prior art semiconductor sensors. A problem with this type of device is that slow phenomena occurs (structural changes in the metal and/or slow adsorption sites for the reaction intermediaries at the interface) which give rise to stability problems and slow responses (hysteresis).

In U.S. Pat. No. 5,273,779 is described a method of fabricating a gas sensor and the product fabricated thereby. The device comprises a substrate, a buffer layer coated on the substrate, a pair of electrodes disposed on the gas sensing layer, at least one gas sensing layer arranged on the buffer layer and a catalytic layer coated on the gas sensing layer. However the device is not a field effect device but based on conductivity changes in the sensing layers. Additionally the buffer layer is used to prevent reaction between the gas sensing layer and the substrate, i.e. the buffer layer has no function in the gas detection.

In U.S. Pat. No. 4,337,476 is described a method using silicon-rich suicides. Silicon-rich silicides of titanium and tantalum formed by sintering a cosputtered alloy with silicon to metal ratio of three are replacing polysilicon as the gate metal in semiconductor integrated circuits. The technique is used as a normal contact forming procedure in for example standard field effect devices.

In U.S. Pat. No. 4,816,888 is disclosed a way to produce a normal known contact by means of a titanium-gold film. This has nothing to do with the gas sensitivity of the sensor which is based on a moisture sensitive layer.

There is still a demand for a gas sensor array having improved stability and speed of response for use also at high ambient temperatures for instance in a combustion system. A short description of the invention The present invention discloses a gas sensitive semiconductor device suitable for forming arrays having one or more elements containing at least two layers disposed onto a semiconductor substrate, the layers offering better long term stability and faster response compared to elements having only one layer. The layer in contact with the gas to be detected is catalytically active while underlying layers primarily do not have to be catalytic, but at least providing changes in the electric field outside the semiconductor in the presence of the gas to be detected. The sensing electrode may be operated up to about 1000° C. and is therefore of interest for gas sensitive devices based on e.g. siliconcarbide or diamond capable of operation at higher temperatures than that for silicon based devices.

According to a first object of the present invention is provided a gas sensing array comprising at least one sensing device on a semiconductor substrate, wherein changes in the electric field outside the semiconductor occur due to a catalytic layer in contact with the gas to be measured and a mono or multi layer between the catalytic layer and the semiconductor substrate constitutes an intermediate layer in the process of detecting gas, whereby the intermediate layer is different from the catalytically active layer, and has an electrical conductivity making it suitable as an electric contact in the semiconductor device.

According to a second object of the present invention is provided a gas sensing array comprising at least one sensor device on a semiconductor substrate, wherein the substrate is provided with a layer of catalytic metal and changes in the electric field outside the semiconductor occur due to a second catalytic layer in contact with the gas to be measured, and a mono or multi layer, between the catalytic layer and the catalytic metal, whereby the mono or multi layer constitute an intermediate layer in the process of detecting gas, the intermediate layer being different from the catalytic metal layer and the catalytically active layer and may also have electrical properties making it suitable as a part of the semiconductor device.

According to a third object of the present invention the catalytic layer and intermediate layer are deposited on an insulator layer, preferably an oxide, primarily deposited onto the semiconductor substrate to form a field effect structure, such as a field effect transistor, a metal-insulator-semiconductor capacitor, metal thin insulator semiconductor diode, Schottky barrier device or a tunneling device.

According to a fourth object of the invention the catalytically active material consists of catalytic metals, alloys or compounds, oxides, ceramics or polymers, and the intermediate layer is silicide, for example tantalum silicide.

According to a fifth object of the present invention the semiconductor device is fabricated using wide band-gap semiconductor material having band-gap being at least 1.5 eV, for example silicon carbide or diamond.

According to a sixth object of the present invention is provided a method of fabricating a gas sensor array comprising at least one gas sensitive semiconductor device including a suitably doped semiconductor substrate, having the steps of application by evaporation or sputtering, preferably by DC-magnetron sputtering through a mask, of a first mono or multi layer onto the substrate, which layer forms an intermediate layer, whereby this first layer together with a catalytic layer in contact with the gas to be measured is generating a change in the electric field outside the semiconductor and has electrical properties making it suitable as a part of the semiconductor device, and application in the same way of a second layer being catalytically active, consisting of catalytic metals, alloys or compounds, oxides, ceramics or polymers on top of the first layer or layers.

According to a seventh object of the present invention is provided a method of fabricating a gas sensor array comprising at least one gas sensitive semiconductor device including a suitably doped semiconductor substrate provided with a catalytic metal layer, having the steps of application by evaporation or sputtering, preferably by DC-magnetron sputtering through a mask, of a first mono or multi layer onto the catalytic metal layer, whereby this first layer together with catalytic layers is generating a change in the electric field outside the semiconductor, and application in the same way of a second layer being catalytically active, consisting of catalytic metals, alloys or compounds, oxides, ceramics or polymers, on top of the first layer or layers.

According to an eight object of the present invention is included in the method a further step of application of a third layer in advance of the application of any further layers, this third layer being an insulator, preferably an oxide layer, onto the semiconductor substrate, to form a field effect device, such as a field effect transistor, a metal-insulator-semiconductor capacitor, metal thin insulator semiconductor diode, a Schottky barrier device or a tunneling device.

A SHORT DESCRIPTION OF THE DRAWINGS

The invention, together with further objects and advantages thereof, may best be understood by making reference to the following description taken together with the accompanying drawings where like reference numerals refer to same or corresponding elements, in which.

A DESCRIPTION OF AN ILLUSTRATIVE EMBODIMENT

1. Introduction

Figure 3:
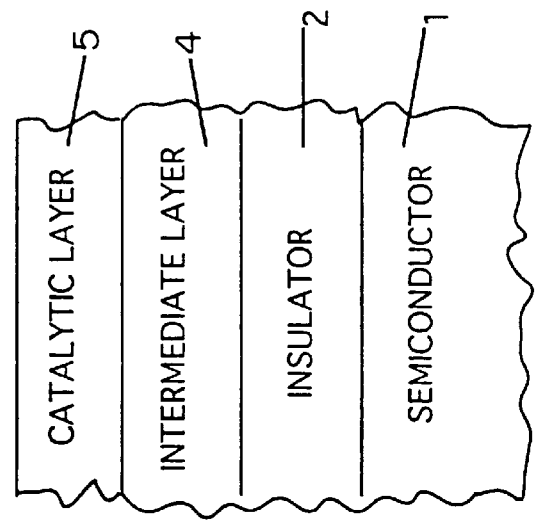
FIG. 3 is a cross section of a gas semiconductor sensor having a two layer structure including an intermediate layer on an insulating layer of a semiconductor substrate according to a second embodiment of the present invention.

Chemical sensors operating at high temperatures are of interest in several types of combustion control. Furthermore for sensors based on the use of catalytic metals as active sensing elements a high temperature means that molecules like saturated hydrocarbons also can be detected. Field effect devices according to the state of the art based on silicon are limited to temperatures below about 250° C. Therefore it has been of interest to develop field effect devices having catalytic metal gates based on silicon carbide as the semiconductor. Silicon carbide, e.g. 6H—SiC, has a band-gap of about 2.9 eV. Field effect devices based on SiC can therefore be operated up to at least 800° C. A platinum-oxide-silicon carbide structure (Pt—MOSiC) can be used to detect hydrogen and (saturated) hydrocarbons at such temperatures as discussed in "Chemical sensors for high temperatures based on silicon carbide", by A. Arbab et al., Sensors and Materials, 4, 4, 1993, pp 173–185, "Gas sensors for high temperature operation based on metal oxide silicon carbide (MOSiC) devices", by A. Arbab et al., Sensors and Actuators B, 15–16, 1993, pp 19–23, and "Evaluation of gas mixtures with high-temperature gas sensors based on silicon carbide", by A. Arbab et al., Sensors and Actuators B, 18–19, 1994, pp 562–565, which hereby are refered to. Arbab was previously the name of the present inventor Baranzahi.

The high temperature operation of the sensors caused, however, also some problems related e.g. to the stability of the catalytic metal gate. A phenomenon called catalytic etching may occur during reactions between hydrogen containing molecules and oxygen on catalytic metals at temperatures above 450° C. which is discussed for example by V. W. Dean et al., in J. Phys. Chem. 92, 1988, pp 5731–5738. Further more there may be changes in the structure of the catalytic metal. These phenomena can change the area of the metal contact and hence cause a long term drift of the sensor signal. Field effect devices according to the state of the art have also often slow adsorption sites for the reaction intermediary at the catalytic metal insulator interface causing drift and/or hysteresis phenomena.

Here will, however be disclosed a method to fabricate a device which shows a fast response and a good stability both during operation and storage as well as a description of the actual component intended for a gas sensing array.

2. Forming a gas sensitive device

In the discussion will be referred to metal oxide silicon carbide capacitors (MOSiC) for the explanation although the ultimate device and preferred embodiment may be a field effect transistor in silicon carbide. The capacitance voltage, C(V)-curve of the MOSiC-structure may for example be recorded using a Boonton bridge at 1 MHz. A feedback circuit is then used to monitor the voltage necessary to maintain a constant pre-set capacitance. The change (decrease) in this voltage upon exposure to the molecules to be detected is the response of the device. The observed voltage shift is caused by polarization phenomena in the metal-oxide structure. For thick catalytic metal contacts, like those used in the prior devices, the polarization is most probably due to hydrogen atoms at the metal-insulator interface and/or in the insulator.

In an experimental setup three substrates were prepared as follows: Silicon carbide (6H—SiC) wafers, n-type (nitrogen doped to $1.6 \cdot 10^{18}$ cm$^{-3}$) with a 10 $\mu$m n-type silicon carbide epilayer ($1.55 \cdot 10^{16}$ cm$^{-3}$), were purchased from Cree Research, Inc., Durham, N.C., USA. A wafer was cleaned in a solution of $H_2O+H_2O_2$+ammonia, 5:1:1 for 5 minutes at 80° C., rinsed in deionized (DI) water, cleaned in $H_2O$+ $H_2O_2$+HCl, 6:1:1 for 5 minutes at 80° C. and rinsed in DI water. The native oxide was etched in concentrated HF (40%) for 5 minutes. Thereafter the wafer was rinsed in DI water, dried and oxidized in dry oxygen at 1250° C. for 3.5 hours and annealed in argon at the same temperature for 30 minutes. The oxide thickness was 135±4 nm as measured by ellipsometry. The oxide on the back of the wafer was etched in buffered HF while the front side was protected by photoresist. After removing the photoresist an ohmic back contact of 150 nm TaSi$_x$ and 100 nm Pt was deposited by DC-magnetron sputtering with a substrate temperature of 350° C. The Pt coating of TaSi$_x$ is for protection of the back contact from oxygen in subsequent high temperature measurements in air. The gate electrode was formed through a shadow mask of copper. The substrate was heated to 350° C. during sputtering in order to improve adhesion of Pt to SiO$_2$, since it has been suggested that Pt sticks better to a SiO$_2$ surface at elevated temperatures. Three types of gate electrode was formed as follows. Substrate No. 2 remained at room temperature during the evaporation.

Figure 1:
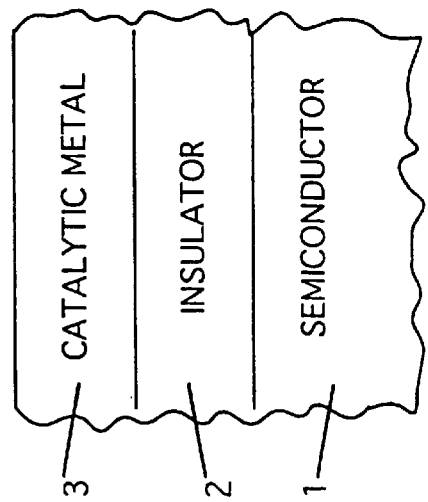
FIG. 1 is a cross section of a prior art gas semiconductor sensor having a one layer structure on a semiconductor substrate with an insulating layer.

Substrate of sample 1 received 300 nm Pt, DC-magnetron sputtered through a copper mask having a diameter of 1.5 mm with substrate temperature 350° C. during sputtering. (One layer structure of prior art according to FIG. 1)

Substrate of sample 2 received 0.3 nm Cr+300 nm Pt, electron gun evaporation through a copper mask having a diameter 1.0 mm and no external heating of the substrate. (Two layer structure corresponding to the prior art sample 1)

Substrate of sample 3 received 50 nm Pt+50 nm TaSi$_x$+100 nm Pt, DC-magnetron sputtered through a copper mask having a diameter of 1.0 mm with substrate temperature 350° C. during sputtering. (Three layer structure of the present invention according to FIG. 2)

Figure 2:
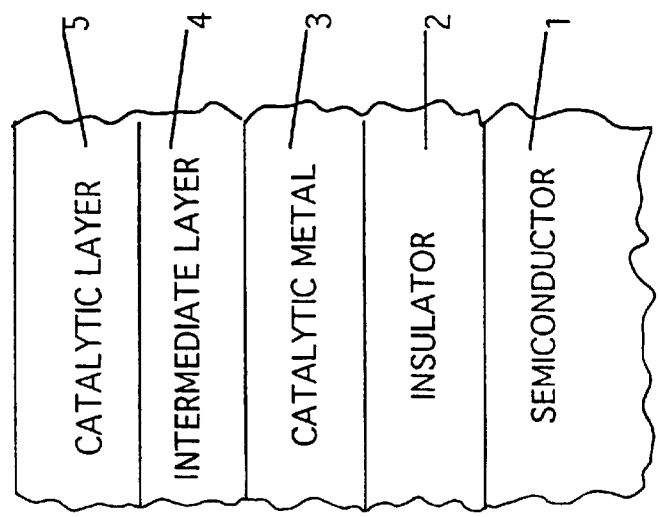
FIG. 2 is a cross section of a gas semiconductor sensor having a three layer structure including an intermediate layer on top of a catalytic metal on top of an insulating layer on a semiconductor substrate according to a first embodiment of the present invention.

FIG. 2 shows a schematic picture of the structure of the sample 3 MOSiC substrate of the present invention.

The samples were then mounted on a platinum foil (contacted to ground by a platinum wire) in a small quartz cylinder placed inside a closed quartz tube about 50 cm in length and 5 cm in diameter inside a furnace, where the temperature could be varied between room temperature and 1100° C. with a precision of ±4° C. The gate electrode was contacted by a platinum probe through a quartz piston inside the quartz cylinder. Gases were supplied to the samples through another quartz tube 5 mm in diameter. A computerized gas mixing system was used to mix gases in desired concentrations from a few ppm to several percent. Argon was used as the carrier gas and all gases were of 99.99% purity or better. The total gas flow was 100 ml/min and the total pressure was about one atmosphere or slightly above.

The samples were activated by operating them at 550° C. (in an atmosphere consisting of pulses of hydrogen and ethane in argon and oxygen) for 24 hours. At the activation procedure it is presumed that the composition of the Pt—TaSi$_x$—Pt part of the structure undergoes changes. Measurements were then carried out at temperature from 350 to 700° C. in steps of or 50° C. Below 350° C. the response time may be quite long for some molecules.

3. General experimental observations

Figure 4:
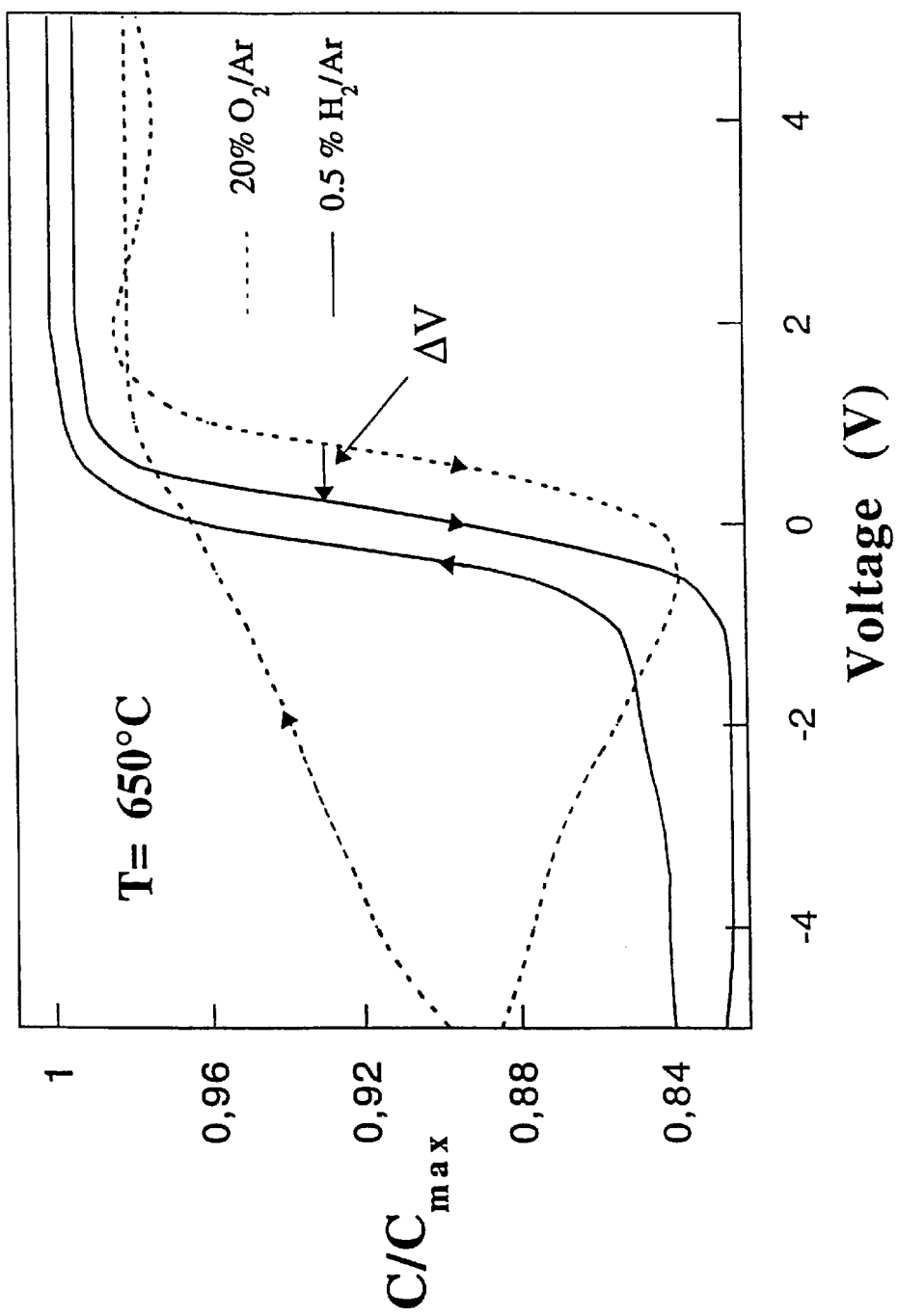
FIG. 4 shows an example of C(V)-curves recorded at 650° C. for a three layer MOSiC device according to FIG. 2.

C(V)-curves (at 650° C.) for the sample 3 being the three layer gate MOSiC device are shown in FIG. 4. The curve to the right is obtained when the sensor is operated in synthetic air, 20% O$_2$ in Ar. The next curve to the left is due to 5000 ppm H$_2$ in argon. The shift of the C(V)-curve indicated as ΔV in the flat-band region is the response of the device to hydrogen. The time dependence of ΔV was obtained using a fast recorder and using the constant capacitance technique mentioned in our chapter of 'Forming a gas sensitive device'.

The set of curves in FIG. 4 illustrates some of the features observed on such a MOSiC device at sufficiently high temperatures. For many devices the capacitance in the inversion region shows a large hysteresis in oxygen (or pure argon), a hysteresis which disappears in the presence of hydrogen. Furthermore there is often a hysteresis in the position of the C(V)-curves obtained for increasing potential on the metal contact (see FIG. 4). When monitoring ΔV at a fixed capacitance the problems of the hysteresis effects are much smaller or does not occur since such measurements are made with a constant electric field at the semiconductor surface.

The long term stability at 550° C. of the sample 1 was checked for eight days and changes in the response could be seen on a time scale of 4–6 hours. The sample 2, being a two layer structure having the thin chromium layer beneath the platinum film was used to test if an increased adhesion of the metal to the oxide could provide an even more stable gate. It was, however, found in agreement with previous studies on Pd-metal oxide silicon devices that the hydrogen and hydrocarbon sensitivity disappeared in the presence of the chromium layer. (Also see "Hydrogen induced drift in palladium gate metal-oxide-semiconductor structures", by C. Nylander et al., J. Appl. Phys., 56, 4, 1984, pp 1177–1188.)

The best result from the above 3 samples was found in sample 3 with the three layer structure. It had a stable response to hydrogen and hydrocarbons over long periods of time although its gate also shows structural changes. The increased stability of the sensor response can be explained if in principle only the top layer changes structure which means that the gate metal area in contact with the oxide does not decrease like in the case for the prior one layer Pt-gate. Achieved stability demonstrated that the response is almost the same after 12.5 hours of continuous operation at 600° C. and storage in (laboratory) air does not change the response of the device. Further test demonstrated that the response was reasonably fast although there is a slow part especially during the discharge of the device.

Also the temperature dependence of the response to ethane (C$_2$H$_6$) in different oxygen concentrations of a three layer gate structure was tested. The fact that the response in oxygen at intermediate temperatures saturates at a level significantly lower than the response in argon indicates the presence of (at least) two different reaction pathways for the species causing the observed voltage shift. The voltage shift is most probably due to hydrogen atoms at the Pt-oxide interface.

The devices need an activation after fabrication as described above. The time necessary for this activation depends on the thickness of the intermediate layer. This intermediate layer undergoes changes (structural and/or compositional) during the activation.

We then have found one way of increasing the long-term stability and decreasing the time constant for the response. This is achieved by introducing an "intermediate layer" according to FIGS. 2 or 3, where this layer has the following properties after the activation step:

it lets a reaction intermediary through, and it stops structural degrading changes of the layers in contact with the insulator/semiconductor.

According to FIG. 3 the "intermediate layer" should also preferably:

have electrical properties making it suitable as a part of the semiconductor device, give rise to electrical polarization phenomena (electric field changes) in the presence of the reaction intermediary, and only give rise to fast adsorption sites for the reaction intermediary (time constants $\leq$3 sec.).

Preferred embodiments

A first preferred embodiment of the sensing device of the present invention, shown in FIG. 3, is a two layer structure comprising a first catalytically active material 5 consisting of catalytic metals, alloys or compounds, oxides, ceramics or polymers, a second intermediate layer 4 constituted of silicide preferably a tantalum silicide, deposited on an insulator layer 2 on a semiconductor substrate 1, preferably having a wide band-gap semiconductor material, said band-gap being at least 1.5 eV. Such wide band-gap materials being for example silicon carbide or diamond. The device is preferably fabricated using the technique discussed for the preparation of the test sample 3 above but excluding the Pt-layer on top of the insulator corresponding to a layer not realized in this first preferred embodiment.

Thus a substrate according to the first preferred embodiment should starting-from a suitable substrate, for example silicon carbide or diamond, for example prepared as described in a preceding paragraph, receive in sequence 50 nm TaSi$_x$+100 nm Pt, DC-magnetron sputtered through a copper mask having a diameter of 1.0 mm with substrate temperature 350° C. during sputtering. (A two layer structure of the present invention.)

A second preferred embodiment of the sensing device of the present invention, shown i FIG. 2, is thus a three layer structure comprising a first catalytically active material 5 consisting of catalytic metals, alloys or compounds, oxides, ceramics or polymers, a second intermediate layer 4 constituted of silicide, preferably a tantalum silicide, and a third layer 3 of catalytic metal, deposited on an insulator layer 2 on a semiconductor substrate 1, preferably having a wide band-gap semiconductor material, said band-gap being at least 1.5 eV. Such wide band-gap materials being for example silicon carbide or diamond. The device is preferably fabricated using the technique discussed for the preparation of the test sample 3 above. The layer 3 of catalytic metal may also serve as a contact for the gas sensitive device.

A substrate according to the second preferred embodiment should starting from a suitable substrate for, example silicon carbide or diamond, be prepared in the same manner as for the first preferred embodiment, receive in sequence 50 nm Pt+50 nm TaSi$_x$+100 nm Pt, DC-magnetron sputtered through a copper mask having a diameter of 1.0 mm with substrate temperature 350° C. during sputtering. (A two layer structure of the present invention.)

We advise at the moment a deposition method like sputtering as being the preferred method of applying the different layers of the invention.

Instead of a semiconductor field effect device as described we also foresee that other types of components well may be provided with this described type of gate, for example a metal-insulator-metal tunneling diode as the electric current through such a device also is affected by the polarization effects in the gate electrode, i.e. the electric field at the insulator surface.

The desired properties for the intermediate layer can be achieved in different ways and with different materials, for instance it may be achieved by sandwiching different layers onto each other in order to allow the different materials to contribute with different properties.

One can also consider the possibility of the intermediate layer being formed through interdiffusion or reaction between at least two of the sandwiched layers the outer catalytic layer combining with the layer under it to give an intermediate layer.

The intermediate layer may also be electrically insulating or conducting.

The intermediate layer also serves to protect the device from degrading structural changes. The device described here arranged in an array makes it very applicable as a combustion sensor. They are especially useful at small oxygen concentrations, where the sensitivity can be controlled by the temperature of the device. The devices according to the present invention are fast enough for such desired applications.

What is claimed is:

1. A method of fabricating a gas sensor array comprising at least one gas sensitive semiconductor device including a suitably doped semiconductor substrate (1), comprising the steps of:

comprising wide band-gap semiconductor material having a band-gap of at least 1.5 e.v.;

providing a first layer semiconductor substrate (1);

applying onto said first layer semiconductor substrate (1) by evaporation or sputtering, a second layer insulator layer (2);

applying onto said second layer insulator layer (2) by evaporation or sputtering, a third layer mono- or multi-layer intermediate layer (4) which comprises a silicide; and applying onto said third layer mono- or multi-layer intermediate layer (4) by evaporation or sputtering, a fourth layer catalytic layer (5).

2. A method of fabricating a gas sensor array according to claim 1, further comprising the step of applying by evaporation or sputtering, a catalytic metal layer (3) before applying said mono- or multi-layer intermediate layer (4).

3. The method according to claim 1, wherein the insulator layer (2) comprises an oxide.

4. The method according to claim 1, wherein the wide band-gap semiconductor material comprises a member selected from the group consisting of silicon carbide and diamond.

5. The method according to claim 1, wherein said intermediate layer (4) is subjected to an annealing step.

6. The method of claim 5, wherein the annealing step is carried out a temperature of at least 500° C.

7. The method according to claim 1, wherein said intermediate layer (4) comprises a silicide.

8. The method according to claim 7, wherein the intermediate layer (4) comprises tantalum silicide.

9. A gas sensing array comprising at least one sensing device, wherein said sensing device comprises:

a first layer semiconductor substrate (1);

comprising wide band-gap semiconductor material having a band-gap of at least 1.5 e.v.;

a second layer insulator layer (2) disposed on said first layer semiconductor substrate (1);

a third layer intermediate layer (4) comprising a silicide, and disposed on said second layer insulator layer (2); and a fourth layer catalytic layer (5) disposed on said third layer intermediate layer (4);

wherein said fourth layer catalytic layer (5), when in contact with a gas to be measured, changes an electric field outside said first layer semiconductor substrate (1); and said mono- or multi-layers of the third layer intermediate layer (4) are different from said fourth layer catalytic layer (5).

10. A gas sensing array according to claim 9, further comprising a catalytic metal layer (3)

disposed between said second layer insulator layer (2) and said third layer intermediate layer (4), wherein said third layer intermediate layer (4) is different from said catalytic metal layer (3) and said fourth layer catalytic layer (5).

11. The gas sensing array according to claim 9, wherein said layers form a field effect structure selected from the group consisting of: a field effect transistor, a metal-insulator-semiconductor capacitor, a metal thin insulator semiconductor diode, a Schottky barrier device and a tunneling device.

12. The gas sensing array according to claim 11, wherein the insulator layer (2) comprises an oxide.

13. The gas sensing array according to claim 9, wherein the catalytic layer (5) comprises a member selected from the group consisting of: a catalytic metal, a catalytic alloy, a catalytic oxide, a catalytic ceramic compound and a catalytic polymer compound.

14. The gas sensing array according to claim 9, wherein the semiconductor material comprises a member selected from the group consisting of silicon carbide and diamond.

15. The gas sensing array according to claim 9, wherein the intermediate layer (4) is subjected to an annealing step.

16. The gas sensing array according to claim 9, wherein said intermediate layer (4) comprises a silicide.

17. The method according to claim 1 further comprising the step of applying an insulator layer (2) onto said semiconductor substrate (1), before the application of additional layers, wherein the combined layers form a field effect device selected from the group consisting of: a field effect transistor, a metal-insulator-semiconductor capacitor, a metal thin insulator semiconductor diode, a Schottky barrier device and a tunneling device.

18. The method according to claim 1, wherein the catalytic layer (5) comprises a member selected from the group consisting of a catalytic metal, a catalytic alloy, a catalytic oxide, a catalytic ceramic compound and a catalytic polymer compound.

19. The gas sensing array according to claim 15, wherein the annealing step is carried out at a temperature of at least 500° C.

20. The gas sensing array according to claim 16, wherein said intermediate layer (4) comprises tantalum silicide.

21. A gas sensing array according to claim 9, wherein the intermediate layer (4) is an electrically conductive contact for the semiconductor device.

22. The gas sensing array according to claim 9, wherein the intermediate layer (4) is non-catalytic.

* * * * *